United States Patent
Xu et al.

(10) Patent No.: US 9,226,496 B2
(45) Date of Patent: Jan. 5, 2016

(54) BIOMIMETIC ADHESIVE AND PREPARATION METHOD AND APPLICATION THEREOF

(75) Inventors: Changqing Xu, Beijing (CN); Jun Chen, Beijing (CN); Liuying Yu, Foshan (CN)

(73) Assignees: Institute of Medicinal Plant Development The Chinese Academy of Medical Sciences, Beijing (CN); Foshan Sanshui Xianghai Adhesive Co., Ltd., Foshan, Guangdong Province (CN)

( * ) Notice: Subject to any disclaimer, the term of this patent is extended or adjusted under 35 U.S.C. 154(b) by 99 days.

(21) Appl. No.: 13/989,873

(22) PCT Filed: Nov. 29, 2010

(86) PCT No.: PCT/CN2010/079249
§ 371 (c)(1),
(2), (4) Date: Sep. 26, 2013

(87) PCT Pub. No.: WO2012/071698
PCT Pub. Date: Jun. 7, 2012

(65) Prior Publication Data
US 2014/0186286 A1    Jul. 3, 2014

(51) Int. Cl.
| | | |
|---|---|---|
| A01N 25/24 | (2006.01) | |
| C08F 220/18 | (2006.01) | |
| C09J 133/10 | (2006.01) | |
| A01N 43/80 | (2006.01) | |
| A01N 63/02 | (2006.01) | |

(52) U.S. Cl.
CPC ............ *A01N 25/24* (2013.01); *C08F 220/18* (2013.01); *C09J 133/10* (2013.01)

(58) Field of Classification Search
None
See application file for complete search history.

(56) References Cited

U.S. PATENT DOCUMENTS

| | | | | |
|---|---|---|---|---|
| 4,418,120 | A * | 11/1983 | Kealy et al. | 428/343 |
| 5,234,517 | A | 8/1993 | Pape et al. | |
| 5,707,638 | A * | 1/1998 | Losel et al. | 424/407 |
| 6,080,418 | A * | 6/2000 | Sengupta et al. | 424/408 |
| 6,242,528 | B1 * | 6/2001 | Clark et al. | 524/560 |
| 6,505,434 | B1 | 1/2003 | Kloczko et al. | |
| 2002/0164364 | A1 * | 11/2002 | Quong | 424/417 |
| 2010/0247684 | A1 * | 9/2010 | Reid et al. | 424/725 |
| 2010/0254917 | A1 * | 10/2010 | Brouns et al. | 424/55 |

FOREIGN PATENT DOCUMENTS

| | | |
|---|---|---|
| CN | 1147228 C | 4/2004 |
| CN | 1242672 C | 2/2006 |
| CN | 1911012 | 2/2007 |
| CN | 101044851 | 10/2007 |
| CN | 100360630 C | 1/2008 |
| CN | 201075956 Y | 6/2008 |
| CN | 101845282 | 9/2010 |
| EP | 0258753 B1 * | 3/1988 |
| JP | 55-011546 | 1/1980 |
| JP | 2009249539 | 10/2009 |
| KR | 100959909 | 5/2010 |

OTHER PUBLICATIONS

Compendium of herbicide adjuvants (1998): Winfield solutions, LLC.[retrieved on Mar. 17, 2015 from on-line website: http://www.herbicide-adjuvants.com/cgi-bin/adjdb.cgi?db=adjproductview&Company=Winfield%20Solutions%2C%20LLC&view_records=1&sb=3&so=ascend&nh=2].*

Machine English translation of KR 100959909 (Mar. 2015).*

* cited by examiner

*Primary Examiner* — Ernst V Arnold
*Assistant Examiner* — Kyung Sook Chang

(57) ABSTRACT

Disclosed is a biomimetic adhesive belonging to prevention and treatment of plant pest. The components and ratio of raw materials thereof are as follows: 25-50% of soft acrylic monomer, 1-5% of acrylic monomer, 0.1-0.3% of nonionic emulsifier, 0.1-0.8% of anionic emulsifier, 0.2-0.6% of catalyst, 0.1-0.3% of antiseptic, 0.02-0.05% of defoamer, and deionized water as remainder. Fluorescent substances or insect pheromones can also be added to said biomimetic adhesive. The biomimetic adhesive of the present invention has good effect of insect sticking without environmental impact, has long time effect, is safe, non-toxic and non-polluting, and can be sprayed directly onto the surface of plant branch and leaves using an ordinary sprayer due to its low viscosity at room temperature. It also has no adverse effects on photosynthesis and normal growth of plants. The preparation method of the biomimetic adhesive is also disclosed.

8 Claims, No Drawings

BIOMIMETIC ADHESIVE AND PREPARATION METHOD AND APPLICATION THEREOF

PRIORITY CLAIM

This is a national stage of PCT/CN2010/079249 filed Nov. 29, 2010, the entirety of which is incorporated herein by reference.

TECHNICAL FIELD

The present invention belongs to the field of prevention and treatment of plant pests, and concretely relates to a biomimetic adhesive having insect sticking effect, and to the method of preparation of the biomimetic adhesive and the use thereof.

BACKGROUND ART

One of the major hindrances for high and stable yields in the agricultural production is harmful organisms, such as various pests, pathogenic microorganisms, and the like. Especially, a variety of small pests are one of the difficult points for prevention and treatment in practical production due to the large magnitude of occurrence and strong adaptability and likeness to develop drug resistance. At present, the main measurement for preventing and treating harmful organisms is by chemical means. However, such method is prone to the problem of pesticide residue, which not only leads to severe contamination of environment, but also destroys the biodiversity of the ecosystem.

An alternative approach for preventing and treating harmful organisms is by physical means, wherein pest-sticking adhesives are used in the prevention and treatment of pest, which are free of the problem of pesticide residue and environment pollution. Currently used pest-sticking adhesives are mainly of three types: (1)Type 1: those oily adhesives in gel or semisolid state at ambient temperature (5-40° C.), mainly composed of components such as rosin, paraffin or pblybutene, added with castor oil or other organic solvent and generally incorporated with thickening agents and the likes. Such pest-sticking adhesives are of high viscosity, such as those disclosed in CN 200410008453, CN 200510014730, CN 200510064422, and CN 200720006978. This type of pest-sticking adhesive can only be applied by means of brush application or must be painted on substrate materials such as paperboard, color disk, plastic paper and the like, and can exert a better pest sticking effect only if they are used together with other pest inducing substances (such as sexual pheromones). The main problem of such adhesives lie in that: due to their toxic actions on plant, they cannot be applied directly to tender tissues of plants such as branches and leaves; secondly, they cannot be applied by spraying due to their high viscosity, and thus involve inconvenient application and low prevention and treatment efficiency. (2)Type 2: Those in liquid state at room temperature, with main component of organic solvent, such as the pest-sticking adhesive with polyacrylamide and Turkey red oil(sulfonated castor oil) as main ingredients, such as those disclosed in CN 200610025325, for adhering pest in locations such as refuse dump. The main problems of such pest-sticking adhesives are: inadaptability to be sprinkled directly to tender tissues of plants such as branches and leaves since they are harmful to plant tissues; secondly, the organic solvent contained therein may pollute environment. (3)Type 3: Pest-sticking adhesives in liquid state at room temperature, which dries quickly after being sprayed. For example, JP 84023352 and JP 53124181 disclose the spraying agents comprising resin derivatives, polyterpene derivatives, such as natural or synthetic rubbers, poly-(iso)butylene, lanolin and the like, and organic solvent (cyclohexylamine, aromatic hydrocarbons such as xylene, benzene, halogenated hydrocarbons), as well as atomizing agent (such as dimethyl ether), as the main ingredients. JP 55011546 and JP 82057001 disclose the pest-sticking adhesive having a film formation property at a low temperature, with vinyl acetate resin and low toxicity solvents as main ingredients. The features of this type of quick drying pest-sticking adhesives are that, the viscous components cure promptly after spraying the adhesive onto the bodies of pests at room temperature (25° C.), which immobilizes the appendages of the pest, such as feet and wings, and thereby deprives the moving ability of the pest. The problem of this type of pest-sticking adhesive lies in that (a) they can exert pest sticking effect, only if they are sprayed directly onto the bodies of the pests; (b) the viscous components lose their viscous property within several minutes after spraying application, and thus cannot retain the pest sticking capability for long duration; (c) the volatile solvent component may pollute environment; and (d) they cannot be sprayed on the surface of plants such as branches and leaves, since they are harmful to plant tissues. As a result, this type of pest-sticking adhesive can only be used in the prevention and treatment of pest in habitable room.

Chinese patent CN 99120025.X discloses a pest-sticking adhesive consisting of polyvinyl alcohol, water soluble silicate, surfactant, polyvinylpyrrolidone and water, which cures promptly within several minutes after spraying application to immobilize the appendages of pests such as feet and wings, and deprive the moving ability of the pests, and thereby reduce the damage from pests. However, the pest-sticking adhesive similarly involves the following problems: they must be sprayed directly onto the bodies of pests to effectively immobilize the pests; secondly, the viscous components lose their potency rapidly, and the validity period for sticking pest is short. Thus, they need frequent spraying to achieve the expected effects, which is labor intensive and material waste and has a high cost.

DISCLOSURE OF THE INVENTION

The first object of the present invention is to provide a biomimetic adhesive having pest-sticking property, the biomimetic adhesive has a good effect of pest sticking and a long effect duration, and can be sprayed onto the stalks and leaves of plants without adversely affect the normal growth of plants.

Another object of the present invention is to provide a method of preparation the above mentioned biomimetic adhesive.

Yet another object of the present invention is to provide the use of the above mentioned biomimetic adhesive.

In order to realize the above objects, the present invention provides the following embodiments.

The biomimetic adhesive of the present invention has the following components and their ratios by mass: 25-50% of soft acrylic monomer, 1-5% of acrylic monomer, 0.1-0.3% of nonionic emulsifier, 0.1-0.8% of anionic emulsifier, 0.2-0.6% of catalyst, 0.1-0.3% of antiseptic, 0.02-0.05% of defoamer, and deionized water as remainder.

The soft acrylic monomer in the above biomimetic adhesive is one of ethyl acrylate, ethyl methacrylate, butyl acrylate, butyl methacrylate, octyl acrylate, isooctyl acrylate, methyl methacrylate or isobutyl methacrylate, or mixture of them.

The acrylic monomer in the biomimetic adhesive refers to acrylic acid or methacrylic acid.

The nonionic emulsifier in the biomimetic adhesive is one of nonyl phenol polyoxyethylene ether, fatty alcohol polyoxyethylene ether mixture, polyether-modified trisiloxane, or mixture of them.

The anionic emulsifier in the biomimetic adhesive is one of fatty alcohol polyoxyethylene ether sodium sulfate, alkyl ether sulfate, alkaryl ether sulfate or succinic ester sulfonate, or mixture of them.

The catalyst in the biomimetic adhesive is inorganic peroxides, preferably such as sodium persulfate, ammonium persulfate, or potassium persulfate.

The antiseptic in the biomimetic adhesive is such as isothiazolinone compounds, or bronopol compounds. Such as the water soluble antiseptics such as US Rohm & Haas Kathon®LXE bactericide(5-chloro-2-methyl-4-isothiazolin-3-one+2-methyl-4-isothiazolin-3-one), Bronopol(2-bromo-2-nitro-1,3-propylene glycol, $C_3H_6BrNO_4$).

The defoamer in the biomimetic adhesive includes water soluble defoamers such as polysiloxane compounds (such as defoamers of polydimethyl siloxane (silicone)(organosilicon), CYCLO METHYL SILOXANEs), polyether compounds (such as polypropylene oxide glycerol ether), mineral oil defoamer (such as polyether mineral oil defoamers, nonsilicone mineral oil defoamers, polyether silicone oil mineral oil defoamer).

The following components may be further added into the biomimetic adhesive: at least one of fluorescent substances or insect pheromones, wherein the fluorescent substances may be added in a ratio of 0.1-5% by mass, and the insect pheromones may be added in a ratio of 0.01-0.1% by mass.

The fluorescent substances include long fluorescent lag noctilucent powder, such as alkaline earth aluminate based-or silicate based light storing and emitting materials, zinc sulfide or calcium sulfide series fluorescent powder, preferably rare earth aluminate based or rare earth silicate based noctilucent powder.

The insect pheromone is at least one of insect sexual pheromone, aggregation pheromones or warning pheromone.

A method of preparation of the above biomimetic adhesive, including the following steps:
(1) Adding deionized water, anionic emulsifier, soft acrylic monomer and acrylic monomer into reaction vessel 1 in proportions, followed by stirring at 40-60 rpm for 15-20 minutes, to obtain an emulsion; wherein the added amount of deionized water is 7-25% by mass relative to the total amount of deionized water to be added, and the added amount of anionic emulsifier is 70-90% by mass relative to the total amount of anionic emulsifier to be added;
(2) Adding deionized water, anionic emulsifier, and catalyst into reaction vessel 2, followed by stirring at 70-90° C. and 40-50 rpm for 10-15 minutes, the reaction vessel 2 is stirred all along at 40-50 rpm; wherein the added amount of deionized water is 70-88% by mass relative to the total amount of deionized water to be added, the added amount of anionic emulsifier is 10-30% by mass relative to the total amount of anionic emulsifier to be added, and the added amount of catalyst is 10-20% by mass relative to the total amount of catalyst to be added;
(3) Extracting 5-30% by mass of emulsion from reaction vessel 1 and injecting it into reaction vessel 2 followed by stirring for 10-15 minutes;
(4) Dissolving catalyst in deionized water; dropwise adding the residual emulsion left in reaction vessel 1 into reaction vessel 2 over 3-4 hours, and meanwhile dropwise adding the dissolved catalyst over 20-30 minutes; after the completion of the addition, holding the temperature for 50-70 minutes, wherein the added amount of the deionized water is 5-23% by mass relative to the total amount of the deionized water to be added; the added amount of the catalyst is 80-90% by mass relative to the total amount of the catalyst to be added; and the amount of the said residual emulsion is 70-95% by mass relative to the total amount of the emulsion;
(5) Cooling the reaction vessel 2 to 40-50° C., adding to reaction vessel 2 with antiseptic, defoamer, nonionic emulsifier in proportions, followed by stirring for 10-15 minutes and filtering through 80-100 mesh, collecting the filtrate to obtain the biomimetic adhesive.

The added amount of deionized water in the above step (1) of the above preparation method is preferably 10-15% by mass of the total amount of deionized water to be added.

The anionic emulsifier in the step (1) of the above preparation method is preferably sodium dodecyl sulfate or sodium dodecyl benzene sulfonate.

The added amount of the anionic emulsifier in the step (I) of the above preparation method is preferably 80% by mass relative to the total amount of anionic emulsifier to be added.

The soft acrylic monomer in the above step (1) of the above preparation method is preferably butyl acrylate and/or isooctyl acrylate.

The acrylic monomer in the step (1) of the above preparation method is preferably acrylic acid.

The added amount of anionic emulsifier in the step (2) of the above preparation method is preferably 20% by mass relative to the total amount of anionic emulsifier to be added.

The reaction temperature in the step (2) of the above preparation method is preferably 80-85° C.

The proportion of the emulsion extracted in step (3) of the above preparation method is preferably 10-15% by mass.

The proportion of the emulsion extracted in step (4) of the above preparation method is preferably 85-90% by mass.

The time period for holding the temperature in step (4) of the above preparation method is preferably 60 minutes.

In the preparation method of the above biomimetic adhesive, fluorescent substances are added into the above prepared biomimetic adhesive in a proportion of 0.1-5% by mass, stirring to homogeneity, filtering through 100 mesh filter screen, and then sealing for use.

The fluorescent substances in the above preparation method is preferably rare earth aluminate based noctilucent powder.

In the preparation method of the biomimetic adhesive of the present invention, the biomimetic adhesive is added prior to use with insect pheromone in proportion of 0.01-0.1% by mass, followed by stirring to homogeneity.

The biomimetic adhesive of the present invention can be directly sprinkled onto the branches and leaves of the target plant by means of spraying, and forms adhesive drips on the surface of the branches and leaves. These drips can retain their stickability for tens of days or even several months and form "mine field" for sticking pests, and thereby intercept the normal behaviors of pest such as food ingestion, reproduction, and inhabit so as to inhibit the propagation of the pest population and thereby achieve the purposes of preventing plant from pests.

The long fluorescent lag fluorescent materials contained in the biomimetic adhesive of the present invention absorb solar energy in daytime and emit lights of different colors (wavelengths) in night time, which, together with the odor of the plant, enhances the inducing effect to pests and thereby improve pest sticking effect of the biomimetic adhesive.

The biomimetic adhesive of the present invention can be sprayed to the overwinter or oversummer locations of the pests for lowering the base number of the overwintering and oversummering pests by adhering the pest in overwintering and oversummering forms or prevent them from arriving to the overwintering or oversummering locations, and thereby achieve the purpose of lowering the damage of pest on target plants.

The biomimetic adhesive of the present invention can also be sprayed onto various color disks to form adhesive drips thereon, for trapping pest having tropism to certain color, and thereby protect the target plants from the damage by pests.

As compared to the pest-sticking adhesives known in the art, the biomimetic adhesive of the present invention has the following advantages: (1) the biomimetic adhesive of the present invention is an aqueous based adhesive using water as solvent, without any organic solvent, which makes the biomimetic adhesive of the present invention safe, nonpoisonous and pollution-free; (2) the biomimetic adhesive of the present invention shows high contact sticking capability and good wetting property, and thus can stick any part of the pest such as feet, antenna, wings by only slight touch; (3) the biomimetic adhesive of the present invention can withstand the influence from wind, rain, and sunshine, possesses UV and weather resistance, and can exert pest sticking effect for a long time period;(4) the biomimetic adhesive of the present invention shows low viscosity at ordinary temperature (10-40° C.) and thus can be sprayed directly onto the branches and leaves of plants by common agroatomizer, and will not adversely affect the normal photosynthesis and normal growth of the plants, and can be simply applied; (5) the fluorescent substances or insect pheromone contained in the biomimetic adhesive of the present invention may improve the attraction to pests and thereby enhance the pest prevention and treatment effect; (6) the preparation method of the biomimetic adhesive of the present invention is simple and has a low cost.

DETAILED DESCRIPTION OF THE INVENTION

The present invention is further illustrated by incorporating the following examples, which, however, by no means limits the protection scope of the present invention.

EXAMPLE 1

The Preparation of the Biomimetic Adhesive

The components of the raw materials of the biomimetic adhesive included: butyl acrylate 25 kg, isooctyl acrylate 20 kg, acrylic acid 1 kg, sodium dodecyl sulfate, 200 g, ammonium persulfate 200 g, biocide C25 (isothiazolone compounds) 10 g, silicone deformer 20 g, nonyl phenol polyethylene oxide ether (OP-10) 100 g, deionized water 53.47 kg, and further added violet aluminate long fluorescent lag noctilucent powder 1 kg and thrips sexual pheromones 1 g.

The procedure of the Preparation method was as follows:
(1) Adding deionized water 8.5 kg, sodium dodecyl sulfate 140 g into reaction vessel 1, followed by adding butyl acrylate 25 kg, isooctyl acrylate 20 kg and acrylic acid 1 kg, the content of the reaction vessel 1 was stirred at 40 rpm for 15 minutes, to obtain an emulsion of about 54.64 kg;
(2) Adding deionized water 41.0 kg, sodium dodecyl sulfate 60 g, ammonium persulfate 20 g into reaction vessel 2, stirring the content in the reaction vessel 2 at 70° C. and 50 rpm for 15 minutes; the reaction vessel 2 was stirred at 50 rpm all along during the polymerization reaction;
(3) Extracting the emulsion 5 kg from reaction vessel 1 for directly injecting into the polymerization reaction vessel 2, followed by stirring for 15 minutes;
(4) Dissolving ammonium persulfate 180 g with deionized water 3.97 kg to obtain an ammonium persulfate solution; dropwise adding the residual emulsion in reaction vessel 1 into reaction vessel 2 over 3 hours and meanwhile dropwise adding the ammonium persulfate solution over 30 minutes; the content of reaction vessel 2 was stirred at 50 rpm all along during the course of addition;
(5) Holding the temperature of the reaction vessel 2 for 60 minutes after the completion of the addition; cooling to 50° C., and adding biocide C25 (isothiazolone compound, Zhejiang Best Chemical Company Ltd., Zhejiang Quzhou) 10 g, silicone defoamer 20g, nonyl phenol polyoxyethylene ether (OP-10) 100 g, followed by stirring for 10 minutes and filtering through 100 mesh filter screen, to obtain the filtrate, that is, the biomimetic adhesive.

The above prepared biomimetic adhesive was added with violet aluminate long fluorescent lag noctilucent powder (such as the MH and MH-W series product available from Lanxi Minhui Optic and Electronic Co., Ltd, Zhejiang Lanxi, or LMS series product available from Dalian LumingLihgt Co. Ltd., Liaoning Dalian) 1 kg, and then was sufficiently stirred to homogeneity and filtered through 100 mesh filter screen. The filtrate was collected to obtain fluorescent powder containing biomimetic adhesive, which was sealed for use.

The above prepared fluorescent powder containing biomimetic adhesive was added prior to use with thrips sexual pheromones 1 g, and then sufficiently stirred to homogeneity to obtain insect sexual pheromones containing biomimetic adhesive.

EXAMPLE 2

The Preparation of Biomimetic Adhesive

The components of the raw materials of the biomimetic adhesive included: butyl acrylate 30 kg, methyl methacrylate 16 kg, methacrylic acid 3 kg, sodium dodecyl sulfate 600 g, potassium persulfate 400 g, Bronopol fungicide 10 g, mineral oil deformer 100 g, nonyl phenol polyethylene oxide ether (OP-10) 300 g, deionized water 49.59 kg.

The procedure of the Preparation method was as follows:
(1) Adding deionized water 10 kg, butyl acrylate 30 kg, methyl methacrylate 16 kg, methacrylic acid 3 kg, sodium dodecyl sulfate 480 g into reaction vessel 1, followed by stirring at 50 rpm for 20 minutes, to obtain an emulsion of about 59.48 kg;
(2) Adding deionized water 35.0 kg, sodium dodecyl sulfate 120 g, potassium persulfate 80 g into reaction vessel 2, stirring the content in the reaction vessel 2 at 80° C. and 45 rpm for 10 minutes; the reaction vessel 2 was stirred at 45 rpm all along during the polymerization reaction;
(3) Extracting the emulsion 9.0 kg from reaction vessel 1 for injecting into the reaction vessel 2, followed by stirring for 10 minutes;
(4) Dissolving potassium persulfate 320g with deionized water 4.59 kg to obtain a potassium persulfate solution; dropwise adding the residual emulsion in reaction vessel 1 into reaction vessel 2 over 4 hours and meanwhile dropwise adding the potassium persulfate solution over 30 minutes;

(5) Holding the temperature of the reaction vessel 2 for 50 minutes after the completion of the addition; cooling to 50° C., and adding Bronopol fungicide 10 g, mineral oil defoamer 100g, nonyl phenol polyoxyethylene ether (OP-10) 300 g, followed by stirring for 12 minutes and filtering through 100 mesh filter screen, collecting the filtrate to obtain the biomimetic adhesive.

EXAMPLE 3

The Preparation of Biomimetic Adhesive

The components of the raw materials of the biomimetic adhesive included: butyl methacrylate 30 kg, octyl acrylate 20 kg, acrylic acid 5 kg, alkyl ether sulfate 800 g, sodium persulfate 600 g, HUAKE-108 (2-n-octyl-4-isothiazolin-3-one) fungicide 10 g, silicone deformer 200 g, nonyl phenol polyethylene oxide ether (OP-10) 300 g, deionized water 43.09 kg; further added aluminosilicate long fluorescent lag fluorescent powder 4 kg.

The procedure of the Preparation method was as follows:
(1) Adding deionized water 10 kg, alkyl ether sulfate 560 g, butyl methacrylate 30 kg, octyl acrylate 20 kg, and acrylic acid 5 kg, into reaction vessel 1, followed by stirring at 40-60 rpm for 20 minutes, to obtain an emulsion of about 65.56 kg;
(2) Adding deionized water 30 kg, alkyl ether sulfate 240 g, ammonium persulfate 90 g into reaction vessel 2, stirring the content in the reaction vessel 2 at 70-90° C. and 50 rpm for 15 minutes; the reaction vessel 2 was stirred at 50 rpm all along during the polymerization reaction;
(3) Extracting the emulsion 18 kg from reaction vessel 1 for directly injecting into the polymerization reaction vessel 2, followed by stirring for 15 minutes;
(4) Dissolving ammonium persulfate 510 g with deionized water 3.09 kg to obtain an ammonium persulfate solution; dropwise adding the residual emulsion in reaction vessel 1 into reaction vessel 2 over 3 hours and meanwhile dropwise adding the ammonium persulfate solution over 20 minutes;
(5) Holding the temperature of the reaction vessel 2 for 60 minutes after the completion of the addition; cooling to 50° C., and adding HUAKE-108 (2-n-octyl-4-isothiazolin-3-one) fungicide 10 g, silicone defoamer 200 g, nonyl phenol polyoxyethylene ether (OP-10) 300 g, followed by stirring for 10 minutes;
(6) Adding aluminosilicate long fluorescent lag fluorescent powder 4 kg, followed by stirring to homogeneity; filtering through 100 mesh filter screen, collecting the filtrate to obtain fluorescent powder containing biomimetic adhesive.

EXAMPLE 4

Determination of an Adhesion Property of the Biomimetic Adhesive

The key index of the property of the biomimetic adhesive was its initial adhesion property, which was tested by Chinese national standards GB/T 4852-2002, Test method for tack of pressure sensitive adhesive tapes by rolling ball, method B: skewed slot rolling ball method.
Concrete operations are as follows:
(1) Specimen preparation: coating a biomimetic adhesive onto a chipboard (Guangdong Junda Paper Industry Ltd.) of 25 mm wide and 150 mm long in an adhesive film thickness of 10-15 μm. Before the test, the specimens were left for horizontally standing in 23° C. and 50% relative humidity for 2 hours. The tested specimens were biomimetic adhesives prepared in the above Examples 1, 2, and 3.
(2) Fixing the specimens with the adhesive facing upward at the prescribed position in a BF-NX-770 adhesive tape initial adhesion property tester (DongWan Beier test equipment Ltd.). The tilt angle of the inclined slot is 21°30'. Placing the rolling ball (14# steel ball with a Diameter of 11.112 mm) at the prescribed initial position, operating the control lever to allow the rolling ball to roll down and measuring the distance when the ball stops rolling. The distance was defined as the length from the terminal of the inclined slot to the center point of the rolling ball contacting the adhesive surface when the ball stops. The test was repeated for 3 times. The average value of the 3 tests represented the initial adhesion property of the biomimetic adhesive. The results were shown in the following table 1, indicating that the biomimetic adhesive of Example 1 resulted in the shortest rolling distance, and thus had the biggest initial adhesion property; while the biomimetic adhesive of Example 3 resulted in the longest rolling distance, and thus has the lowest initial adhesion property. A smaller detection value means that the biomimetic adhesive has a bigger initial adhesion property and a higher sensitivity. The adhesive drip can stick a pest when its body slightly contacts the adhesive, which means that the adhesive is effective even to small pests. On the contrary, a larger detection value means that the biomimetic adhesive has a smaller initial adhesion property and a lower sensitivity. The adhesive drip can only stick a pest when its body contacts the adhesive with a relative larger force, which means that the adhesive is only effective to a larger pest and is less effective to a smaller pest.

TABLE 1

Results of the initial adhesion property test of biomimetic adhesives

| Biomimetic adhesive source | rolling distance |
| --- | --- |
| Biomimetic adhesive prepared in Example 1 | 35 mm |
| Biomimetic adhesive prepared in Example 2 | 55 mm |
| Biomimetic adhesive prepared in Example 3 | 65 mm |

EXAMPLE 5

Comparative Test Using Biomimetic Adhesive for Preventing and Treating Thrips (Psilothrips Indicus Bhafti) and Wood Louse (Paratrioza Sinica Yang & Li) in Chinese Wolfberry Garden (I) Experimental Design:
Treatment: the biomimetic adhesive prepared in Example 1 was used, prior to use added with thrips sexual pheromones (Zhangzhou Enjoy technology development Ltd.), followed by mixing to homogeneity. Dosage: 40 kg/667 m$^2$.
Control 1: deionized water, dosage 50 kg/667 m$^2$.
Control 2: pest sticking liquid prepared according to the method of CN 200610025325.0 (Adhesive coagulation liquid, and its application), comprising polyacrylamide 5% and Turkey red oil 95%, mixed to homogeneity. Dosage:40 kg/667 m$^2$.
(I) Test procedure: selecting a Chinese wolfberry garden of 5 years old Chinese wolfberry trees under normal management, random selection of 20 trees for each treatment, sprinkled with common agroatomizers from the crown in the last ten-day period of May. Starting from the first day after the spraying, net photosynthesis rate(P) of the functional leaves of the middle crown of the trees receiving different treatment was determined at 10:00-11:00 in the morning every day by using a LI-6400 Photosynthesis System (produced by LI-COR company, US), 20 leaves for each treatment were measured, for 7 consecutive days, calculating average values for each treatment. After two weeks, 10 trees are examined for each treatment, five leaves selected respectively from the east, west, south, north positions of each tree were examined, and the quantities of thrips (Psilothrips indicus Bhafti) and wood louses (Paratrioza sinica Yang & Li) sticked on the leaves were counted and the average values and standard deviations of the number of pest on leaves were calculated.

TABLE 2

Comparison of the photosynthetic efficiency of Chinese wolfberry leaves and the pest sticking effect on thrips and wood louse by using biomimetic adhesives

| Treatment | photosynthetic rate of the Chinese wolfberry leaves P (unit: $\mu mol/m^2 \cdot S^1$) | | | | | | | numbers of thrips and wood louse captured at day 14 |
|---|---|---|---|---|---|---|---|---|
| | day 1 | day 2 | day 3 | day 4 | day 5 | day 6 | day 7 | (number of pests/leaf) |
| biomimetic adhesive of Example 1 | 11.09 ± 2.60 | 14.30 ± 2.33 | 13.68 ± 2.79 | 15.78 ± 3.36 | 13.62 ± 2.22 | 13.23 ± 3.50 | 14.18 ± 2.71 | 1.68 |
| control 1 | 11.47 ± 1.93 | 13.86 ± 2.16 | 13.73 ± 2.82 | 15.74 ± 4.16 | 13.96 ± 2.03 | 13.86 ± 2.91 | 13.96 ± 2.03 | 0 |
| control 2 | leaf withered | leaf withered | leaf seared | leaf seared | leaf seared | leaf seared | leaf seared | 0.02 |

Results are shown in table 2. As compared with control 1, there was no substantial difference between the influence of the treatment using biomimetic adhesive of Example 1 on the photosynthesis of leaves and young shoots of Chinese wolfberry trees and that of control 1, indicating that the biomimetic adhesive of the present invention does not affect the photosynthesis of the leaves of Chinese wolfberry; while the leaves and young shoots of the Chinese wolfberry trees sprayed with the oily adhesive of control 2 withers and sears rapidly and lose their photosynthesis capability.

After two weeks (see table 2), the adhesive drips on the leaves treated with the biomimetic adhesive of Example 1 were still sticking and can continually stick thrips and wood louse, while the leaves and young shoots of the trees treated with control 2, although can also stick some pests in the initial stage, sear and wither rapidly, indicating that control 2 cannot be applied by spraying to the crown. The above results indicate that the biomimetic adhesive of the present invention shows good pest sticking effect and no adverse effect on the photosynthesis of plants.

EXAMPLE 6

Comparative Test Using Biomimetic Adhesive for Preventing and Treating Chinese Wolfberry Gall Midge (II) Experimental Treatment:
Treatment: biomimetic adhesive prepared in Example 2. Dosage, 35 kg/667m².
Control: pest sticking adhesive prepared according to the method of Example 1 of CN 99120025.X, having the following components and their ratios: polyvinyl alcohol 5%, calcium dodecylbenzene sulfonate 2%, sodium silicate 15%, polyvinylpyrrolidone 1%, and water 77%. 200 times dilution before use.

1. Test procedure: selecting Chinese wolfberry garden under normal management but with severe Chinese wolfberry gall midge (Jaapiella sp.) occurrence. A layer of wheat straw was overlaid in the plant pits before the cracking of the worm cocoon of Chinese wolfberry gall midge and then sprayed respectively with 200 times diluted solution of the biomimetic adhesive of Example 2 or control pest sticking adhesive on the surface of the overlaid wheat straw in the tree stumps by common agroatomizer, 20 trees in each treatment. Keeping the status after the sprinkling, and, after the mature larvae of Chinese wolfberry gall midge come out from the cocoon, sampling from four positions (east, south, east, and north respectively) under the crowns of trees indifferent treatment region, with 5 trees for each treatment. The soil until 20 cm depth was taken with a soil sampler of 8 cm diameter for examining the numbers of cocoons of Chinese wolfberry gall midge in the soil.

TABLE 3

Test results of biomimetic adhesive on the prevention and treatment of Chinese wolfberry gall midge (unit: number of pest)

| Test treatment | Repeat 1 | Repeat 2 | Repeat 3 | Repeat 4 | Repeat 5 |
|---|---|---|---|---|---|
| biomimetic adhesive of Example 2 | 1 | 5 | 12 | 0 | 6 |
| control | 75 | 63 | 116 | 69 | 48 | c. Results are shown in table 3. As compared with the control, the biomimetic adhesive of Example 2 led to a significant reduction of the numbers of cocoons of Chinese wolfberry gall midge in the soil, produced by the mature larvae. It was observed that, after the spraying treatment of control, the surface of the wheat straw dried rapidly and lost the pest sticking capability very soon; the treatment of control leads to a film prone to crack. On the other hand, the mature larvae of Chinese wolfberry gall midges had jumping ability, and therefore can pass the gaps of the ground covering and piece soil and cocoon. Thus, the control treatment cannot effectively prevent the mature larvae of Chinese wolfberry gall midges from piercing soil and cocooning. The biomimetic adhesive of the present invention maintains its sticking capability for even several months after the treatment, and thus can stick the mature larvae of Chinese wolfberry gall midge and stop them from jumping and piercing soil, when they drop down on the wheat straw, and thereby the biomimetic adhesive of the present invention lead them to death by exposing to air and losing water. Although a minor of larvae can cocoon, the imago will be adhered by the sticking biomimetic adhesive on the wheat straw when they leave soil and thereby cannot mate and spawn. The above results indicate that the biomimetic adhesive of the present invention shows good and long pest sticking effect.

d. Example 7. Comparative test using color disk treated with biomimetic adhesive for preventing and Treating Whitefly 1. Experimental Design:

Treatment: spraying the biomimetic adhesive prepared in Example 3 onto the two sides of commercially available yellow chipboard (a flint coloured paper, produced by Guangdong Junda Paper Industry Ltd.) by a handheld sprayer.

Control: a commercially available yellow pest sticking paper (double coated pest stickingboard, CN 200820141844.8, available from Cangzhou Jiahe Biotech. Co. Ltd.) is used.

2. Test procedure: The biomimetic adhesive treated yellow chipboard and the control pest sticking yellow paper were respectively cut into plates of 10 cm×10 cm and hanged in a cucumber green house with serve whitefly (Trialeurodes vapor ariorum (Westwood)) occurrence, at a height of 10 cm over the new shoots of cucumber. 9 pieces of plates for each treatment were used and the number of trapped whitefly were checked after 2 days of hanging.

e.

TABLE 4

Comparative test of trapping results of the biomimetic adhesive sprayed on yellow board on whitefly (unit: number of pest)

| Treatment | Repeat 1 | Repeat 2 | Repeat 3 | Repeat 4 | Repeat 5 | Repeat 6 | Repeat 7 | Repeat 8 | Repeat 9 | average |
|---|---|---|---|---|---|---|---|---|---|---|
| biomimetic adhesive of Example 3 | 129 | 7 | 215 | 153 | 103 | 166 | 120 | 114 | 176 | 141.4 |
| control | 65 | 43 | 96 | 68 | 87 | 81 | 79 | 64 | 57 | 71.1 | f. The results were shown in table 4, showing that the number of trapped whitefly by the yellow chipboard sprayed with the biomimetic adhesive of the present invention was about two times larger than that of the commercial pest sticking paper. The biomimetic adhesive of the present invention can not only trap whitefly in day time, but also can show stronger trapping effect in night time due to the yellow fluorescence emitted in night. The above results indicate that the biomimetic adhesive of the present application possesses excellent pest sticking effect.

g. The above Examples are only illustrative of preferred embodiments of the invention, but by no way limit the scope of the present invention. All alternatives resulting from any change, modification, substitution, combination and simplification without departing from the spirit of the invention are all encompassed by the present invention.

The invention claimed is:

1. A biomimetic adhesive, comprising the following components and their ratios by mass: soft acrylic monomer 25-50%, acrylic monomer 1-5%, nonionic emulsifier 0.1-0.3%, anionic emulsifier 0.1-0.8%, catalyst 0.2-0.6%, antiseptic 0.1-0.3%, defoamer 0.02-0.05%, at least one of fluorescent substances and insect pheromone, and deionized water as remainder, wherein said soft acrylic monomer is a combination of butyl acrylate and isooctyl acrylate, and wherein the fluorescent substances are added in a proportion of 0.1-5% by mass, and the insect pheromone is added in a proportion of 0.01-0.1% by mass.

2. The biomimetic adhesive according to claim 1, wherein the acrylic monomer refers to is acrylic acid or methacrylic acid.

3. The biomimetic adhesive according to claim 1, wherein the nonionic emulsifier is one of nonyl phenol polyoxyethylene ether, fatty alcohol polyoxyethylene ether, polyether modified trisiloxane, or mixture of them.

4. The biomimetic adhesive according to claim 1, wherein the anionic emulsifier is one of fatty alcohol polyoxyethylene ether sodium sulfate, alkyl ether sulfate, alkaryl ether sulfate or succinic ester sulfonate, or mixture of them.

5. The biomimetic adhesive according to claim 1, wherein the catalyst is inorganic peroxide, and the inorganic peroxide is sodium persulfate, ammonium persulfate or potassium persulfate.

6. The biomimetic adhesive according to claim 1, wherein the antiseptic is isothiazolinone compounds or bronopol compounds.

7. The biomimetic adhesive according to claim 1, wherein the defoamer is polysiloxane compounds, polyetherb compounds, or mineral oil defoamer.

8. A preparation method of the biomimetic adhesive according to claim 1, comprising the following steps:

(1) adding deionized water, anionic emulsifier, soft acrylic monomer and acrylic monomer into reaction vessel 1 in proportions, followed by stifling at a revolution rate of 40-60 rpm for 15-20 minutes, to obtain an emulsion; wherein the added amount of deionized water is 7-25% by mass relative to the total amount of deionized water to be added, and the added amount of anionic emulsifier is 70-90% by mass relative to the total amount of anionic emulsifier to be added;

(2) adding deionized water, anionic emulsifier, and catalyst into reaction vessel 2, followed by stifling at 70-90° C. and a revolution rate of 40-50 rpm for 10-15 minutes, the reaction vessel 2 is stirred all along at a revolution rate of 40-50 rpm; wherein the added amount of deionized water is 70-88% by mass relative to the total amount of deionized water to be added, the added amount of anionic emulsifier is 10-30% by mass relative to the total amount of anionic emulsifier to be added, and the added amount of catalyst is 10-20% by mass relative to the total amount of catalyst to be added;

(3) extracting 5-30% by mass of emulsion from reaction vessel 1 and injecting it into reaction vessel 2 followed by stirring for 10-15 minutes;

(4) dissolving catalyst in deionized water; dropwise adding the residual emulsion in reaction vessel 1 into reaction vessel 2 over 3-4 hours, and meanwhile dropwise adding the dissolved catalyst over 20-30 minutes; after the completion of the addition, holding the temperature for 50-70 minutes, wherein the added amount of the deionized water is 5-23% by mass relative to the total amount of the deionized water to be added; the added amount of the catalyst is 80-90% by mass relative to the total amount of the catalyst to be added; and the proportion of the residual emulsion relative to the total amount of the emulsion is 70-95% by mass;

(5) cooling the reaction vessel 2 to 40-50° C., adding to reaction vessel 2 with antiseptic, defoamer, nonionic emulsifier in proportions, followed by stirring for 10-15 minutes and filtering through 80-100 mesh, collecting the filtrate to obtain the biomimetic adhesive; and (6) at least one of: (a) adding fluorescent substances into the biomimetric adhesive in a proportion of 0.1-5% by mass, and (b) adding insect pheromone into the biomimetric adhesive in a proportion of 0.01-0.1% by mass.

* * * * *